United States Patent
Pigg et al.

[11] Patent Number: 6,152,893
[45] Date of Patent: Nov. 28, 2000

[54] COMPRESSION DEVICE

[75] Inventors: William Pigg, Elvington; David Houldridge, Badger Hill, both of United Kingdom

[73] Assignee: Smith & Nephew PLC, London, United Kingdom

[21] Appl. No.: 09/171,487

[22] PCT Filed: Apr. 18, 1997

[86] PCT No.: PCT/GB97/01078

§ 371 Date: Mar. 1, 1999

§ 102(e) Date: Mar. 1, 1999

[87] PCT Pub. No.: WO97/39709

PCT Pub. Date: Oct. 30, 1997

[30] Foreign Application Priority Data

Apr. 20, 1996 [GB] United Kingdom ............ 9608231

[51] Int. Cl.⁷ ............................................ A61L 15/00
[52] U.S. Cl. ........................... 602/75; 602/62; 602/64; 602/60
[58] Field of Search ........................ 602/75, 60, 62, 602/64, 65, 74, 61, 77

[56] References Cited

U.S. PATENT DOCUMENTS

| 3,613,679 | 10/1971 | Bijou . |
|---|---|---|
| 3,828,369 | 8/1974 | Swallow . |
| 3,856,008 | 12/1974 | Fowler et al. . |
| 4,240,415 | 12/1980 | Wartman . |
| 4,520,806 | 6/1985 | Miller . |
| 5,074,292 | 12/1991 | Cox . |
| 5,111,806 | 5/1992 | Travis . |
| 5,120,300 | 6/1992 | Shaw . |
| 5,171,310 | 12/1992 | Chisena . |
| 5,254,122 | 10/1993 | Shaw . |
| 5,338,290 | 8/1994 | Aboud . |

FOREIGN PATENT DOCUMENTS

| 0 237 194 | 9/1987 | European Pat. Off. . |
|---|---|---|
| 0 475 811 A1 | 3/1992 | European Pat. Off. . |
| 23 29 371 | 1/1975 | Germany . |
| 36 40 979 A1 | 8/1987 | Germany . |
| 202103 | 12/1988 | Switzerland . |
| WO 92/01759 | 2/1992 | WIPO . |

*Primary Examiner*—Michael A. Brown
*Assistant Examiner*—Lalita Hamilton
*Attorney, Agent, or Firm*—Larson & Taylor PLC

[57] ABSTRACT

A compression device for applying a predetermined compression to a limb including a pliable non-extensible sheet, co-operating fastening parts and a mechanism for indicating changes in compression.

16 Claims, 2 Drawing Sheets

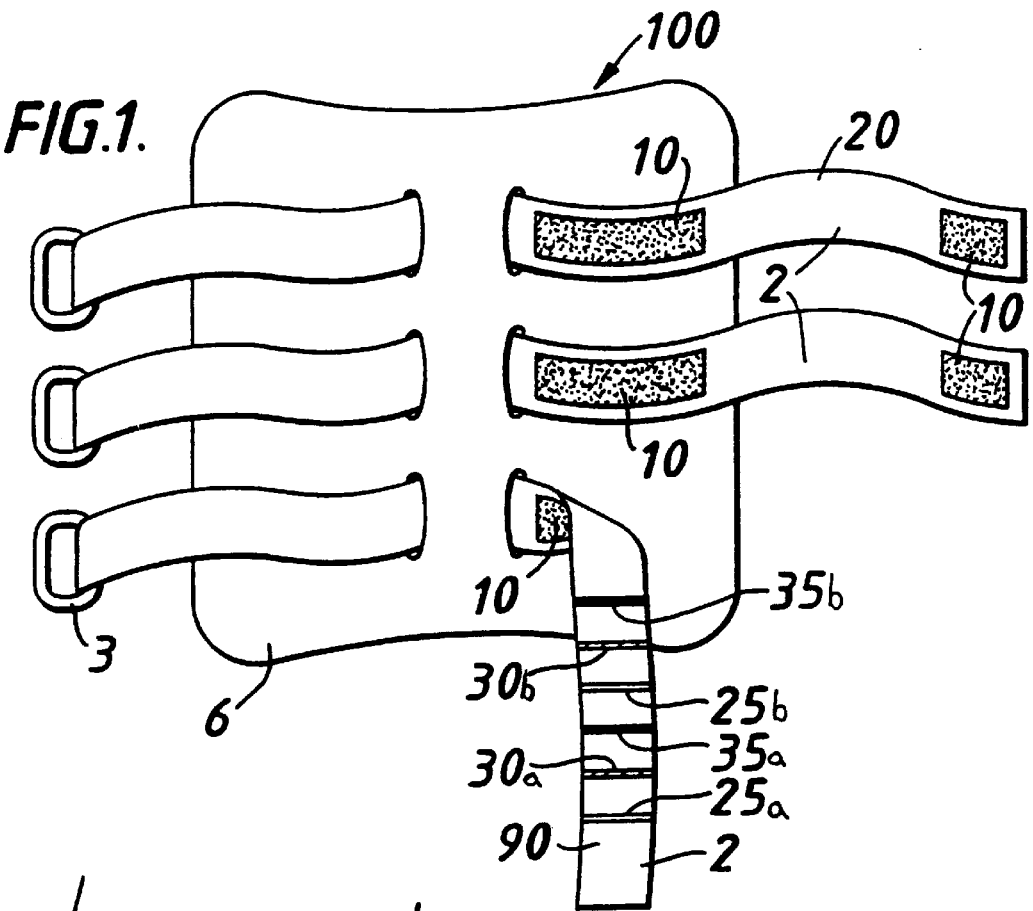
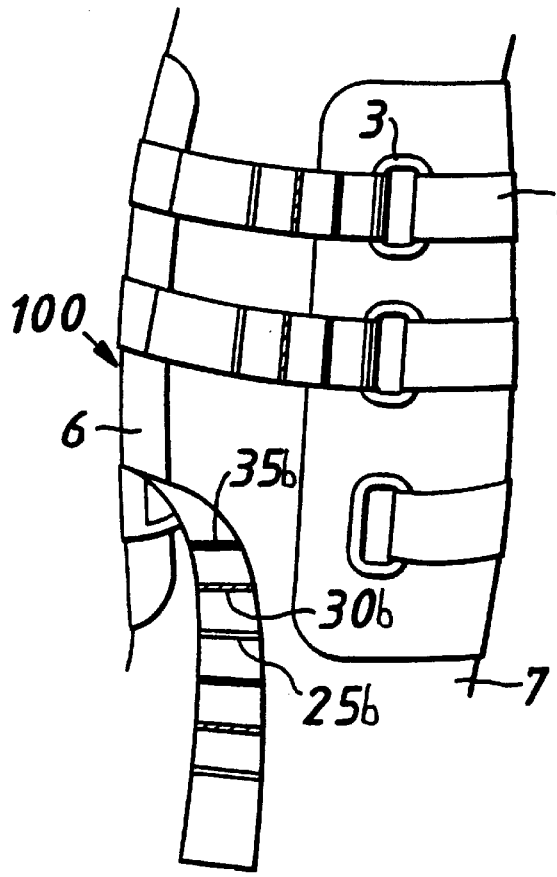

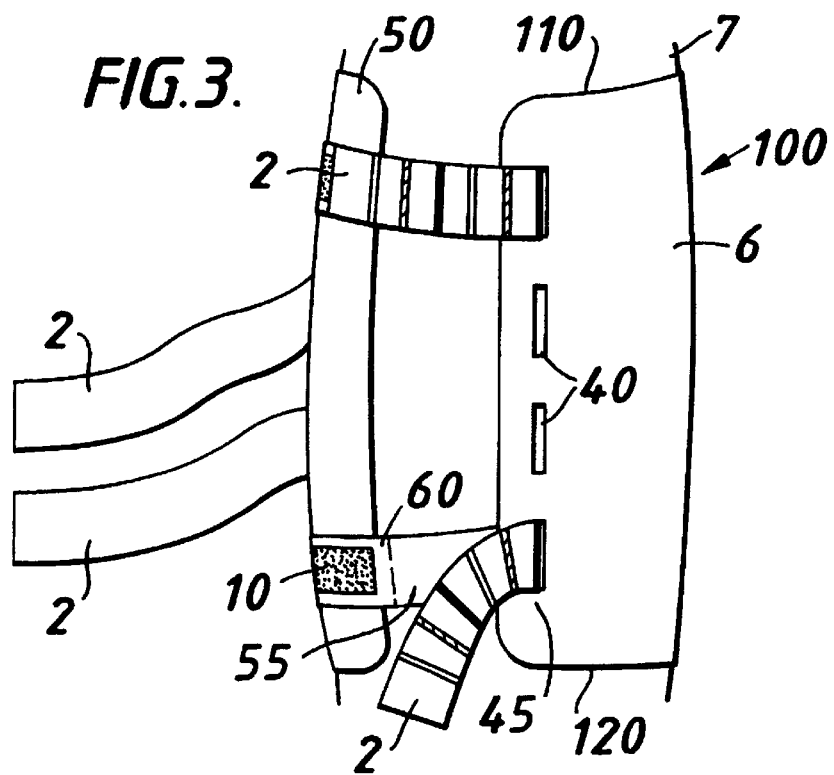
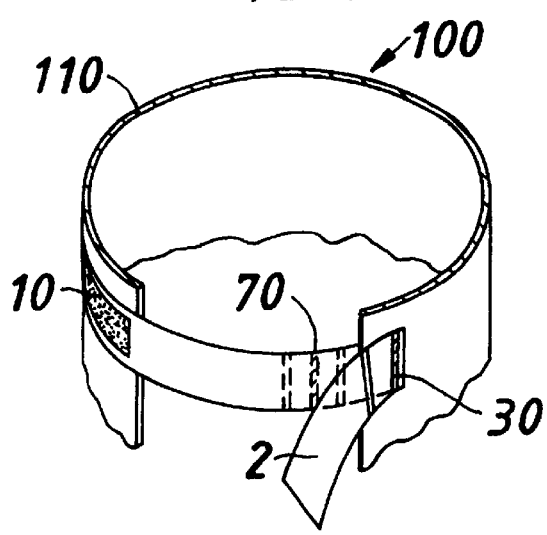
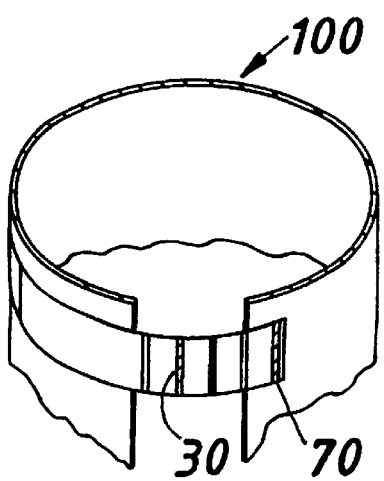

COMPRESSION DEVICE

The present invention relates to a compression device for application to a body portion.

Woven or knitted elastic bandages in both adhesive and non-adhesive forms are used to provide support, to assist in the repair of soft tissues such as healing of strained muscles and in the treatment of various venous conditions. Conventional elasticated woven or knitted bandages have one or more warp yarns which may comprise elastomeric materials such as natural rubber or synthetic elastomeric materials such as polyurethane. Such an elastic support is disclosed in U.S. Pat. No. 3,828,369. It is important that these bandages are applied at a tension which is sufficiently high to enable them to maintain an effective level of compressive force under the bandage over a period of time.

For example, it is known to provide compression bandages having markings which appear as squares when a planar bandage is stretched to a desired degree and which in an unstretched state appear as narrow rectangles.

However, a disadvantage associated with the known woven or knitted bandages is that if they are stretched too much during the application, the compression force under the bandage may be overly great and cause damage, for example by restriction of the blood supply. Furthermore if such a bandage is not stretched enough, little clinical benefit is gained by the application.

In order to alleviate these problems it is known to mark bandages with markings which adopt a particular identifiable configuration when a bandage has been stretched to a certain degree. Such bandages are disclosed in U.S. Pat. No. 3,613,679. Patent Application Nos. EP 0475811, DE 3640979 and DE 2329371. Thus when the configuration is achieved a person applying the bandage may determine that a desired degree of extension has been achieved. However, these bandages suffer from the disadvantage that it is often difficult to assess when a desired degree of extension has been achieved. For example, U.S. Pat. No. 4,520,806 discloses a splint that can be used in different limbs and different limb sizes but does not indicate a suitable degree of compression to be applied.

This is because bandages are applied by different users in different manners and therefore there is considerable variation between users in the degree of overlap of layers of bandage and the angle at which the bandage is applied relative to the longitudinal axis along a body member.

European Patent Application No. 237194 discloses a bandage comprising a rupturable medium containing a liquid or gas which indicates by rupturing if the applied pressure is too great.

Apart from possible staining problems such a bandage would not be reusable, and would only indicate if too much pressure was applied.

Additionally such compression bandages can suffer from stress relaxation, where the pressure is lost soon after application thus reducing any clinical benefit.

A further disadvantage concerns the durability of bandages as hereinbefore described on repeated washing and the lack of ease of application for the patient, especially if the patient is not very flexible.

A legging for compression therapy is described by Vernick et al [Arch. Phys. Med. Rehabil., Vol 68, pp 459, (1987)]. The legging consists of a number of pliable, unyielding, adjustable compression bands, from the knee to the instep. The compression bands can be closed, tightened and opened by the patient.

U.S. Pat. No. 5,338,290 discloses a variable tension medical device comprising multiple strips of elastic material which may be stacked. The straps are wrapped around a limb and then the tension is adjusted subjectively until pain relief is felt by the patient.

U.S. Pat. No. 5,120,300 discloses a compression band with connectors for application to a limb and slide through connectors for applying compression to the limb.

However there are several disadvantages with the use of these devices. As each strap or band is set up individually there is no simple way for setting up a consistent pressure gradient nor is there provided a way for the practitioner or the patient to be able to tell whether or not the required pressure has been achieved.

There is thus a need to provide an effective compression device for applying a predetermined amount of compression to a limb.

According to the present invention there is provided a compression device for applying a predetermined compression to a limb comprising a pliable non-extensible sheet to be wrapped around a limb, where said sheet is provided with a plurality of cooperating first and second fastening parts each along opposing edges of the sheet, thereby to secure the device to the limb, wherein said first fastening part is provided with a plurality of first and second related indicia that visually indicate the relative movement of said first fastening part relative to said second fastening part between the application of zero tension as indicated by said first indicia and the application of a predetermined optimal degree of tension as indicated by said second indicia on fastening said first and second parts to provide compression.

The first and second indica preferably comprise a series of markings on the first fastening part and most preferably the indicia comprise a series of coloured markings.

The pliable non-extensible sheet will herein after be known as a transfer sheet.

The use of a transfer sheet allows transfer of applied tension from the fastening parts to the sheet which in turn transfers an even pressure load across the sheet to the limb.

The transfer sheet may be made from a thermoplastic material, or any other pliable unyielding material. Preferably the material exhibits rigidity longitudinally, but flexibility circumferentially. The transfer sheet will be of suitable dimensions for application to a limb and may be of variable thickness to allow degrees of pliability. The transfer sheet may be made up of a plurality of sections, for example cylinders, struts or stays which may be fitted together to make a fanned raft to facilitate conformability to the limb.

In a preferred embodiment the transfer sheet is made of a thermoplastic material. Suitable thermoplastic materials are described in PCT Application No. WO93/21967, U.S. Pat. No. 4,240,415 and include polymers which soften at temperatures ranging from 40° C. to 100° C. These materials soften under heat, are capable of being moulded into shape with pressure and harden on cooling without undergoing chemical change.

Alternatively sheet materials such as plastics, foams or textile composites (such as shin guard materials) may be employed as the pressure transfer media.

Preferably the transfer sheet is provided with at least two fastening parts, most preferably with three fastening parts.

Fastening parts may comprise straps with buckles, straps fitted through a loop, hoop, buckle or other aperture (as are employed for fastening ski boots), straps with hook and loop fasteners or any other suitable method for fastening two opposing edges of the sheet.

In an embodiment of the present invention there is provided a transfer sheet with a plurality of co-operating first and second fastening parts wherein said first fastening part comprises a strap and said second fastening part comprises an associated aperture.

Further the strap may be provided with fastening means to allow the strap to be held in place after applying the transfer sheet to a limb.

Hook and loop fasteners are commonly known in the art. One brand of hook and loop fasteners is known by the Trade Mark VELCRO™.

Preferably the fastening means comprise VELCRO™.

The aperture may be any suitable for passing a strap through, for example a hoop fitted to one end of a strap which is attached to the sheet, or a hoop fitted to the transfer sheet. Suitably the aperture may be a cleft in the transfer sheet.

The straps may be elastic, inelastic or a mixture where for example a section of the strap is elastic.

The strap may be a continuous strap, fitted to the transfer sheet as to encircle the sheet or aptly a strap with fastening means may be fitted to an edge of the sheet and a second strap with a hoop may be fitted to the opposing edge.

Thus in an embodiment of the invention the transfer sheet is provided with a plurality of hoops along one of the edges of the sheet and a plurality of corresponding straps fixed along the opposing edge at positions corresponding to the positions of the hoops.

Preferably the transfer sheet is provided with at least two straps, most preferably three straps, which are preferably spaced evenly along the sheet, wherein each strap is further provided with indicia for indicating changes in compression.

Preferably the straps are continuous with a first and a second end and encircle the transfer sheet. The first end comprises an elastic section and is provided with the indicia. The second end may be elastic or inelastic and is provided with a suitable aperture, for example a hoop may be fitted onto the second end.

Preferably the indicia to indicate changes in compression comprise markings on the straps.

The indica may be in the form of a series of striations, bars or marks on the strap. In a preferred embodiment the indica may be in the form of coloured lines perpendicular to the longitudinal axis of the strap.

In a further embodiment the strap may be an inextensible strap with a first and second end, encircling the sheet with VELCRO™ fastening means at the first end, and with a hoop at a second end, and the strap may have coloured lines marked on the surface at the first end.

Pressure is applied to a limb by fitting the transfer sheet around the limb, feeding said first strap end with the fastening means through the hoop at the second end, until there is no slack and there is zero tension in the strap. When there is no slack and there is zero tension in the strap the colour showing at the contact point with the hoop is noted and pressure is subsequently applied by tightening the strap to the next line of that same colour, or a colour as indicated by a physician.

The marks are spaced the correct distance apart to allow the user to apply the desired pressure to the limb which for the lower leg is currently considered to be 40 mmHg the ankle and 20 mmHg at the knee.

The distances may be set up, for example, by applying the device to a limb fitted with pressure sensors and marking the points on the straps where there is no slack in the straps and then tightening the straps until the pressure sensor indicates that the desired compression is being applied. A second mark is then made on the strap. This process is then repeated for limbs of varying shapes and sizes.

An alternative method for determining the spacing of the indicia comprises considering the force extension curve of the materials used.

For example if the fastening parts comprise straps encircling the transfer sheet the force extension curve of the straps can be measured using means known in the art. Thus the amount of extension required to apply a given force can be determined from the curve and markings can be applied accordingly at appropriate distances along the straps.

If the fastening parts comprise two discrete parts attached to opposing edges then the force extension curve of that section of the sheet and the fastening parts should be measured.

The use of elastic straps means that more extension is required to apply a certain force than for an inelastic strap. However, this may aid in application of the device as the indicia would be spaced further apart, thus allowing an easier visual assessment.

The marks may be spaced to allow any desired pressure gradient along the limb to be set.

Suitably said compression device as hereinbefore described is a compression brace.

According to the present invention there is also provided a method of treatment for one or more of the following disorders; namely venous disorders, lymphodoema, which comprises applying a device as hereinbefore described to an affected site on a patient.

The present invention will now be described by way of example only with reference to the accompanying drawings.

FIG. 1 shows a plan view of a device according to the present invention in a planar form.

FIG. 2 shows a plan view of the device as shown in FIG. 1, applied to a limb.

FIG. 3 shows a plan view of another embodiment of a device according to the present invention applied to a limb.

FIG. 4 schematically illustrates a perspective view of the upper portion of the device shown in FIG. 3 before compression is applied. The remainder of the device is not shown for clarity.

FIG. 5 schematically illustrates the portion shown in FIG. 4 after compression is applied.

Referring to FIG. 1 an embodiment of the present device 100 of the invention is shown, where a thermoplastic transfer sheet 6 is fitted with encircling straps 2 which have a hoop 3 at one end and graduated markings at the opposite end on the inner surface of the strap 90.

The straps 2 are inelastic and comprise VELCRO™ fastening means 10 on the outer surface 20. The graduated markings comprise coloured (red 25, green 30, blue 35) stripes on the inner surface 90 of the strap, perpendicular to the longitudinal axis of the strap 2 at set distances apart.

FIG. 2 shows device 100 of FIG. 1 fitted to a limb 7 where a thermoplastic transfer sheet 6 is moulded to fit the limb 7 and the straps 2 are threaded through the co-operating hoop 3 until there is no slack and there is zero tension, and the colour showing at the contact point with hoop 3 is noted and the straps 2 are subsequently tightened to the next stripe of the noted colour, to provide a predetermined level of compression.

FIG. 3 shows a further embodiment of the device 100 of the present invention where the device 100 is fitted to a limb 7. The device 100 comprises a thermoplastic transfer sheet 6 with an upper end 110 and a lower end 120 and with clefts 40 provided along one edge 45 of the sheet 6, and straps 2 which do not encircle the device.

Straps 2 are fixed to the opposite edge 50 of the sheet, by any known means such as gluing, lamination, riveting.

Straps 2 comprise an elastic section 55 and an inelastic section 60.

Straps 2 are provided with VELCRO™ fastening means 10.

FIG. 4 shows schematically a perspective view of the upper portion 110 of device 100 as shown in FIG. 3 where the strap 2 is set to be without any slack, at zero tension on green mark 30 and in FIG. 5 the strap 2 is set to the required degree of compression by tightening the strap 2 to show the second green mark 70, and fastening strap 2 using fastening means 10.

What is claimed is:

1. A compression device for applying a predetermined compression to a limb comprising:

a pliable non-extensible sheet to be wrapped around a limb, where said sheet is provided with a plurality of cooperating first and second fastening parts each along opposing edges of the sheet, thereby to secure the device to the limb;

wherein the first fastening part is provided with a plurality of first and a plurality of second indicia with each respective first indicia being associated with a predetermined respective second indicia to provide the predetermined compression by visually indicating the relative movement of said first fastening part relative to said second fastening part between (a) the application of fastening said fastening parts until there is no slack and there is zero tension as indicated by a noted said first indicia showing at a contact point of the first and second fastening parts, and (b) the application of a predetermined optimal degree of tension as indicated by a respective said second indicia associated with the noted said first indicia on fastening showing at the point of contact of said first and second fastening parts to provide compression.

2. A device according to claim 1 where the indicia comprise a series of markings on said first fastening part.

3. A device according to claim 2 where the markings comprise a coloured series.

4. A device according to claim 1 where the first fastening part 2 comprises a strap.

5. A device according to claim 4 wherein the strap is provided with fastening means.

6. A device according to claim 5 wherein the fastening means comprises a hook and loop fastener.

7. A device according to claim 4 where the strap is an inelastic strap.

8. A device according to claim 4 where the indicia comprise a series of coloured lines perpendicular to a longitudinal axis of the strap.

9. A device according to claim 1 where the second fastening part 3 comprises an aperture.

10. A device according to claim 1 wherein said first and second fastening parts comprise a strap with a first and a second end fixed to said sheet wherein said first end is provided with fastening means and indicia and said second end is provided with a hoop.

11. A device according to claim 1 wherein said sheet is made of a thermoplastic material.

12. A device according to claim 1 wherein said first fastening part comprises a strap provided with a series of coloured stripes which comprise said first and second indicia and fastening means; said second fastening part comprises an aperture in said sheet, said series of coloured stripes visually indicate the relative movement of said strap relative to said aperture between the application of zero tension as indicated by a first coloured stripe showing at said aperture and the application by a second coloured stripe by feeding said strap through said aperture and tightening said strap to show said second coloured stripe at said aperture to provide compression.

13. A method for applying predetermined compression to a limb by fitting a device according to claim 1 to a limb characterized by, fastening said fastening parts until there is no slack and there is zero tension in the fastening parts, noting the first indicia showing at a contact point between the first and second fastening parts, and subsequently applying the required pressure by tightening the fastening parts to show the predetermined respective second indicia at the contact point between the first and second fastening part.

14. A method for treating one or more of the following disorders, venous disorders or lymphodoema characterised by applying a device according to claim 1 to an affected limb.

15. Use of a device according to claim 1 as a compression brace.

16. A device according to claim 1 where said first indica (25a, 30a, 35a) are visibly aligned with said second fastening part (3) at zero tension and said second indica (25b, 30b, 35b) are visibly aligned with said second fastening part (3) at a predetermined optimal degree of tension and where misalignment between said second fastening part (3) and said second indica (25b, 30b, 35b) is visually distinct and reveals excessive and insufficient tension applied to said sheet.

* * * * *